US012636278B2

(12) United States Patent
Betts

(10) Patent No.: US 12,636,278 B2
(45) Date of Patent: May 26, 2026

(54) HDAC6-INHIBITED HUMAN REGULATORY T CELLS

(71) Applicant: H. LEE MOFFITT CANCER CENTER AND RESEARCH INSTITUTE, INC., Tampa, FL (US)

(72) Inventor: Brian Betts, Minneapolis, MN (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 763 days.

(21) Appl. No.: 17/759,199

(22) PCT Filed: Jan. 27, 2021

(86) PCT No.: PCT/US2021/015327
§ 371 (c)(1),
(2) Date: Jul. 21, 2022

(87) PCT Pub. No.: WO2021/154882
PCT Pub. Date: Aug. 5, 2021

(65) Prior Publication Data

US 2023/0060230 A1 Mar. 2, 2023

Related U.S. Application Data

(60) Provisional application No. 62/966,241, filed on Jan. 27, 2020.

(51) Int. Cl.
*A61K 31/437* (2006.01)
*A61K 31/416* (2006.01)
*A61K 31/55* (2006.01)
*A61P 37/00* (2006.01)

(52) U.S. Cl.
CPC .......... *A61K 31/437* (2013.01); *A61K 31/416* (2013.01); *A61K 31/55* (2013.01); *A61P 37/00* (2018.01)

(58) Field of Classification Search
CPC .......... A61K 31/437; A61P 37/06; C12Q 1/00
USPC .......................................... 514/292; 435/183
See application file for complete search history.

(56) References Cited

U.S. PATENT DOCUMENTS

| | | | |
|---|---|---|---|
| 9,409,858 | B2 | 8/2016 | Sotomayor et al. |
| 9,751,832 | B2 | 9/2017 | Sotomayor et al. |
| 10,227,295 | B2 | 3/2019 | Sotomayor et al. |
| 2014/0165707 | A1 | 6/2014 | Dahlberg et al. |
| 2015/0056213 | A1 | 2/2015 | Sotomayor et al. |
| 2016/0228434 | A1 | 8/2016 | Reilly et al. |
| 2017/0035710 | A1 | 2/2017 | Sotomayor et al. |
| 2017/0319683 | A1 | 11/2017 | O'Reilly et al. |
| 2019/0022199 | A1 | 1/2019 | Riley et al. |
| 2019/0322983 | A1 | 10/2019 | Rudensky et al. |

FOREIGN PATENT DOCUMENTS

| | | | |
|---|---|---|---|
| WO | 2013/041407 | A | 3/2013 |
| WO | 2013/134467 | A1 | 9/2013 |
| WO | 2014/165707 | A2 | 10/2014 |
| WO | 2015/017546 | A1 | 2/2015 |
| WO | 2016/126721 | A1 | 8/2016 |
| WO | 2016/126722 | A1 | 8/2016 |
| WO | 2016/126724 | A1 | 8/2016 |
| WO | 2016/126725 | A1 | 8/2016 |
| WO | 2016/126726 | A1 | 8/2016 |
| WO | 2016/168598 | A1 | 10/2016 |
| WO | 2016/168660 | A1 | 10/2016 |

OTHER PUBLICATIONS

Bulter, Kyle V., et al., "Rational Design and Simple Chemistry Yield a Superior, Neuroprotective HDAC6 Inhibitor, Tubastatin A," Journal of American Chemical Society, vol. 132, No. 31 (2010), pp. 10842-10846.
Imai, C., et al., "Chimeric receptors with 4-1BB signaling capacity provoke protent cytotoxicity against acute lymphoblastic leukemia," Leukemia, vol. 18 (2004), pp. 676-684.
Kalin, Jay H., et al., "Second-Generation Histone Deacetylase 6 Inhibitors Enhance the Immunosuppressive Effects of Foxp3+ T-Regulatory Cells," Journal of Medicinal Chemistry, vol. 55 (2012), pp. 639-651.
Maher, John, et al., "Human T-lymphocyte cytotoxicity and proliferation directed by a single chimeric TCR/CD28 receptor," Nature Biotechnology, vol. 20 (2002), pp. 70-75.
Sadelain, Michel, et al., "Targeting Tumours with Genetically Enhanced T Lymphocytes," Nature Reviews, vol. 3 (2003), pp. 35-45.
International Search Report and Written Opinion, PCT/US2021/015327, mailed Apr. 22, 2021 (13 pages).
Laino, Andressa S., et al., "HDAC6 selective inhibition of melanoma patient T-cells augments anti-tumor characteristics," Journal for Immuno Therapy of Cancer, vol. 7 (2019) (16 pgs.).
Litjens, et al., "Allogeneic Mature Human Dendritic Cells Generate Superior Alloreactive Regulatory T Cells in the Presence of IL-15", The Journal of Immunology, vol. 194, 2015, pp. 5282-5293.
Oh, et al., "Therapeutic Effect of a Novel Histone Deacetylase 6 Inhibitor, CKD-L, on Collagen-Induced Arthritis in Vivo and Regulatory T Cells in Rheumatoid Arthritis in Vitro", Arthritis Research & Therapy, vol. 19; 154, Jul. 3, 2017, pp. 1-16.

*Primary Examiner* — Charanjit Aulakh
(74) *Attorney, Agent, or Firm* — PABST PATENT GROUP LLP

(57) ABSTRACT

Disclosed are compositions and methods for preventing graft versus host disease (GVHD) or allograft rejection in subjects receiving donor cells. Also disclosed are methods enhancing regulatory T (Treg) cells for use in preventing GVHD. Also disclosed are methods of suppressing alloreactive donor cells in a subject receiving transplant donor cells that involves adoptive transfer of the treated Treg cells. Also disclosed are enhanced Treg cells produced by the disclosed methods that have been engineered to express chimeric antigen receptor (CAR) polypeptide cells.

6 Claims, 15 Drawing Sheets

Summary of antigen specific Treg expansion

| | Treg (Donor B)+HLA-Mismatched Allo DC (Donor A)+IL-2+IL-15 | | |
|---|---|---|---|
| Expansion -1 | DMSO | Tubastatin (1uM) | HDTK032 (2.5uM) |
| Treg cell # | | | |
| Day 0 | 500000 | 500000 | 500000 |
| Day 12 | 1560000 | 2180000 | 2000000 |
| Antigen specific frequency (%) | | | |
| Day 0 | 0.05 | 0.05 | 0.05 |
| Day 12 | 1.34 | 1.51 | 1.631 |
| Antigen specific Tregs | | | |
| Day 0 | 250 | 250 | 250 |
| Day 12 | 20904 | 32918 | 32620 |
| Fold expansion of Day 12 | 84 | 132 | 130 |

FIG. 1D

HDAC6-INHIBITED HUMAN REGULATORY T CELLS

CROSS-REFERENCE TO RELATED APPLICATIONS

This application is a National Stage of International Application No. PCT/US2021/015327, filed Jan. 27, 2021, which claims benefit of U.S. Provisional Application No. 62/966,241, filed Jan. 27, 2020, which is hereby incorporated herein by reference in its entirety.

BACKGROUND

Current immunosuppressive measures to control GVHD or allograft rejection target T cells but compromise post-transplant immunity in the patient.

SUMMARY

Disclosed herein is a method for enhancing regulatory T (Treg) production that involves exposing the Treg cells with an effective amount of an HDAC6 inhibitor and expanding the Treg cells in a culture medium. Also disclosed is a method for producing regulatory T (Treg) cells, that involves purifying $CD4^+$, $CD127^-$, $CD25^+$ Tregs from PBMCs by magnetic bead isolation, stimulating the Tregs with allogeneic monocyte derived DCs, CD3/CD28 beads, or K562 artificial antigen presenting cells, and expanding the Tregs in a culture medium comprising recombinant human (rh)IL-2 (e.g. 10 IU/ml) with or without rhIL-15 (e.g. 10 ng/ml) and an effective amount of an HDAC6 inhibitor for at least 5, 6, or 7 days. For example, in some embodiments, the culture medium includes about 1 μM tubastatin A for at least 5 days.

In some embodiments, the HDAC6 inhibitor selectively inhibits HDAC6 and does not inhibit any other HDACs. In some embodiments, the HDAC6 inhibitor does not inhibit HDAC8. Therefore, in some embodiments, the HDAC6 inhibitor in pan HDAC inhibitor that does not inhibit HDAC8.

A variety of HDAC6 inhibitors have been investigated and are described in Butler et al., J Am Chem Soc 2010, 7J2(31): 10842-10846, and Kalin et al., J Med Chem 2012, 55(2):639-651, which are incorporated by reference in its entirety for HDAC6 inhibitors.

In some embodiments, the HDAC6 inhibitor is a compound described in PCT Patent Publication WO2016/168598, which is incorporated by reference in its entirety for HDAC6 inhibitors. In some embodiments, the HDAC6 inhibitor is a compound described in PCT Patent Publication WO2013/134467, which is incorporated by reference in its entirety for HDAC6 inhibitors. In some embodiments, the HDAC6 inhibitor is a compound described in PCT Patent Publication WO2016/168598, which is incorporated by reference in its entirety for HDAC6 inhibitors. In some embodiments, the HDAC6 inhibitor is a compound described in in PCT Patent Publication WO2013/134467 or WO2015/017546; U.S. Patent Publication No. US2015/0056213 or US2017/0035710; U.S. Pat. Nos. 9,409,858, 9,751,832, or 10,227,295, which are incorporated by reference in their entireties for HDAC6 inhibitors.

In some embodiments, the HDAC6 inhibitor is a compound described in PCT Patent Publication WO2016/126726, WO2016/126725, WO2016/126724, WO2016/126722, or WO2016/126721, which are all incorporated by reference in their entireties for these HDAC6 inhibitors.

In some embodiments, the HDAC6 inhibitor is a compound described in to PCT Patent Publication WO2016/168660, which is incorporated by reference in its entirety for HDAC6 inhibitors. some embodiments, the HDAC6 inhibitor has the chemical formula:

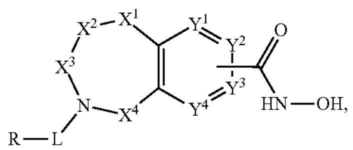

wherein:

X1 is independently CR1R2, NR3, O, or C═O;

X2 and X4 are each independently CR1R2, C═O, S(O) or SO2;

X3 is CR1'R2'; wherein X4, X2, and X1 are not all simultaneously CR1R2;

Y1 and Y4 are not bonded to —C(O)NHOH and are each independently N or CR1;

Y2 and Y3 are each independently N or CR1 when not bonded to —C(O)NHOH and Y2 and Y3, are C when bonded to —C(O)NHOH;

L is —C(O)—, —C(O)(CR1R2)m-, or —C(O)(CR1R2)mO—, wherein L is bound to the ring nitrogen through the carbonyl group;

R is independently, and at each occurrence, —H, —C1-C6 alkyl, —C2-C6 alkenyl, —C4-C8 cycloalkenyl, —C2-C6 alkynyl, —C3-C8 cycloalkyl, —C5-C12 spirocycle, heterocyclyl, spiroheterocyclyl, aryl, or heteroaryl containing 1 to 5 heteroatoms selected from the group consisting of N, S, P, and O, wherein each alkyl, alkenyl, cycloalkenyl, alkynyl, cycloalkyl, spirocycle, heterocyclyl, spiroheterocyclyl, aryl, or heteroaryl is optionally substituted with one or more —OH, halogen, oxo, —NO2, —CN, —R1, R2, —OR3, —NHR3, —NR3R4, —S(O)2NR3R4, —S(O)2R1, —C(O)R', —CO2R1, —NR3S(O)2R1, —S(O)R', —S(O)NR3R4, —NR3S(O)R1, heterocycle, aryl, or heteroaryl containing 1 to 5 heteroatoms selected from the group consisting of N, S, P, and O, with the proviso that R is not bound to L via a nitrogen atom;

each R1 and R2 are independently, at each occurrence, —H, —R3, —R4, –C1-C6 alkyl, —C2-C6 alkenyl, –C4-C8 cycloalkenyl, –C2-C6 alkynyl, –C3-C8 cycloalkyl, heterocyclyl, aryl, heteroaryl containing 1 to 5 heteroatoms selected from the group consisting of N, S, P, and O, —OH, halogen, —NO2, —CN, —NHC1-C6 alkyl, —N(C1-C6 alkyl)2, —S(O)2N(C1-C6 alkyl)2, —N(C1-C6 alkyl)S(O)2R5, —S(O)2C1-C6 alkyl, —(C1-C6 alkyl)S(O)2R5, —C(O)C1-C6 alkyl, —CO2C1-C6 alkyl, —N(C1-C6 alkyl)S(O)2C1-C6 alkyl, or —(CHR5)-NR3R4, wherein each alkyl, alkenyl, cycloalkenyl, alkynyl, cycloalkyl, heterocyclyl, aryl, or heteroaryl is optionally substituted with one or more substituents selected from —OH, halogen, —NO2, oxo, —CN, —R5, —OR3, —NHR3, —NR3R4, —S(O)2N(R3)2, —S(O)2R5, —C(O)R5, —CO2R5, —NR3S(O)2R5, —S(O)R5, —S(O)NR3R4, —NR3S(O)R5, heterocycle, aryl, and heteroaryl containing 1 to 5 heteroatoms selected from the group consisting of N, S, P, and O;

or R1 and R2 can combine with the atom to which they are both attached to form a spirocycle, spiroheterocycle, or a spirocycloalkenyl;

or R1 and R2, when on adjacent atoms, can combine to form a heterocycle, cycloalkyl, cycloalkenyl, aryl, or heteroaryl containing 1 to 5 heteroatoms selected from the group consisting of N, S, P, and O;

or R1 and R2, when on non-adjacent atoms, can combine to form a bridging cycloalkyl, cycloalkenyl, or heterocycloalkyl;

each R1' and R2' are each independently H, aryl, or heteroaryl containing 1 to 5 heteroatoms selected from the group consisting of N, S, P, and O, wherein each aryl or heteroaryl is optionally substituted with one or more substituents selected from —OH, halogen, —NO2, oxo, —CN, —R3, —R5, —OR3, —NHR3, —NR3R4, —S(O)2N(R3)2, —S(O)2R5, —C(O)R5, —CO2R5, —NR3S(O)2R5, —S(O)R5, —S(O)NR3R4, —NR3S(O)R5, heterocycle, aryl, and heteroaryl containing 1 to 5 heteroatoms selected from the group consisting of N, S, P, and O, wherein at least one of R1' or R2' is not H; R3 and R4 are independently, at each occurrence, —H, —C1-C6 alkyl, —C2-C6 alkenyl, —C4-C8 cycloalkenyl, —C2-C6 alkynyl, —C3-C8 cycloalkyl, heterocyclyl, aryl, heteroaryl containing 1 to 5 heteroatoms selected from the group consisting of N, S, P, and O, —S(O)2N(C1-C6 alkyl)2, —S(O)2C1-C6 alkyl, —(C1-C6 alkyl)S(O)2R5, —C(O)C1-C6 alkyl, —CO2C1-C6 alkyl, or —(CHR5)-N(C1-C6 alkyl)2, wherein each alkyl, alkenyl, cycloalkenyl, alkynyl, cycloalkyl, heterocyclyl, aryl, or heteroaryl is optionally substituted with one or more substituents selected from —OH, halogen, —NO2, oxo, —CN, —R5, —O (C1-C6) alkyl, —NHC1-C6 alkyl, N(C1-C6 alkyl)2, —S(O)2N(C1-C6 alkyl)2, —S(O)2NH(C1-C6 alkyl), —C(O)C1-C6 alkyl, —CO2C1-C6 alkyl, —N(C1-C6 alkyl)S(O)2C1-C6 alkyl, —S(O)R5, —S(O)N(C1-C6 alkyl)2, —N(C1-C6 alkyl)S(O)R5, heterocycle, aryl, and heteroaryl containing 1 to 5 heteroatoms selected from the group consisting of N, S, P, and O; R5 is independently, at each occurrence, —H, —C1-C6 alkyl, —C2-C6 alkenyl, —C4-C8 cycloalkenyl, —C2-C6 alkynyl, —C3-C8 cycloalkyl, heterocyclyl, aryl, heteroaryl containing 1 to 5 heteroatoms selected from the group consisting of N, S, P, and O, —OH, halogen, —NO2, —CN, —NHC1-C6 alkyl, —N(C1-C6 alkyl)2, —S(O)2NH(C1-C6 alkyl), —S(O)2N (C1-C6 alkyl)2, —S(O)2C1-C6 alkyl, —C(O)C1-C6 alkyl, —CO2C1-C6 alkyl, —N(C1-C6 alkyl)S(O)(C1-06 alkyl), —S(O)(C1-C6 alkyl), —S(O)N(C1-C6 alkyl)2, —N(C1-C6 alkyl)S(O)(C1-C6 alkyl) or —(CH2)nN(C1-C6 alkyl)2; and each n is independently and at each occurrence an integer from 0 to 6;

each m is independently and at each occurrence an integer from 1 to 6; and provided that when X2 and X4 are both C═O, X1 is not NR3.

In particular, the HDAC6 inhibitor can be the compound (3S)—N-hydroxy-4-(oxane-4-carbonyl)-3-phenyl-2,3,4,5-tetrahydro-1,4-benzoxazepine-8-carboxamide (referred to herein as HDKT032) having the chemical formula:

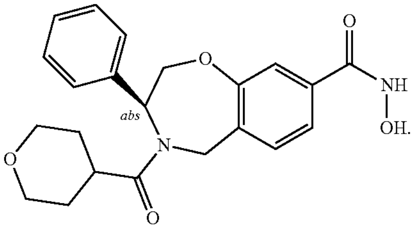 [SMILES: O=C(NO)c1ccc2c(c1)OC[C@H](c1ccccc1)N(C(=O)C1CCOCC1)C2]

In some embodiments, the HDAC6 inhibitor is Tubastatin A (CAS No. 1252003-15-8), which has the following chemical formula:

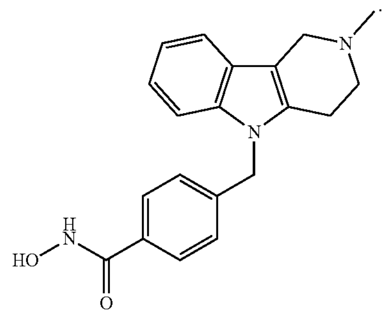 [SMILES: CN1CCc2c(c3ccccc3n2Cc2ccc(C(=O)NO)cc2)C1]

Tubastatin A is a potent and selective HDAC6 inhibitor with $IC_{50}$ of 15 nM in a cell-free assay. Tubastatin A is selective at all isozymes except HDAC8 and maintains over 1000-fold selectivity against all isoforms excluding HDAC8, where it has approximately 57-fold selectivity.

In some embodiments, the HDAC6 inhibitor is Nexturastat A (CAS No. 1403783-31-2), which has the following chemical formula:

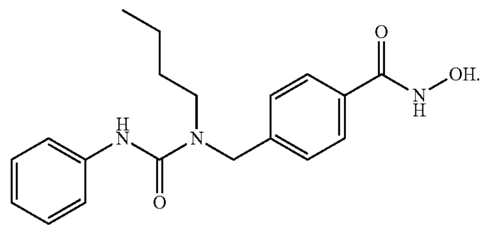 [SMILES: CCCCN(Cc1ccc(C(=O)NO)cc1)C(=O)Nc1ccccc1]

Nexturastat A is a potent and selective HDAC6 inhibitor with $IC_{50}$ of 5 nM, >190-fold selectivity over other HDACs.

In some embodiments, the HDAC6 inhibitor is Nexturastat B (CAS No. 1648893-33-7), which has the following chemical formula:

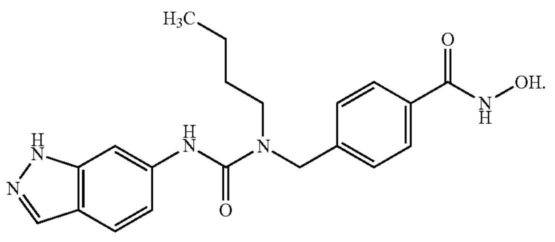 [SMILES: CCCCN(Cc1ccc(C(=O)NO)cc1)C(=O)Nc1ccc2cn[nH]c2c1]

Nexturastat A is a potent and selective HDAC6 inhibitor with $IC_{50}$ of 5 nM, >190-fold selectivity over other HDACs.

In some embodiments, the HDAC6 inhibitor is selected from the group consisting of CAY10603, Tubacin, Rocilinostat (ACY-1215), Nexturastat A, Tubastatin A HCl, Tubastatin A, and HPOB.

In some embodiments, the HDAC6 inhibitor is a gene silencing oligonucleotide, such as a gRNA, siRNA, or miRNA. In some embodiments, the HDAC6 inhibitor is a polypeptide that binds HDAC6 and blocks its activity, such as an aptamer, antibody fragment (e.g. scFv), or soluble receptor. The nucleic acid and amino acid sequences for human HDAC6 are known and can be used to design these inhibitors using routine methods.

Also disclosed are HDAC6-inhibited Tregs produced using the disclosed methods. In some embodiments, the HDAC6-inhibited Tregs are engineered to express a chimeric antigen receptor (CAR) polypeptide to produce HDAC6-inhibited CAR-Tregs.

Also disclosed herein is a method for treating graft versus host disease (GVHD) in a subject that involves isolating regulatory T (Treg) cells from the subject, contacting the Treg cells with an effective amount of an HDAC6 inhibitor, and transferring the HDAC6-inhibited Treg cells back to the subject.

In some embodiments, the tissue transplantation comprises a bone marrow transplantations. In some embodiments, the tissue transplantation comprises a solid organ transplant, including but not limited to, face transplant, abdominal wall transplant, limb transplant, upper extremity transplant, vascularized composite allograft, or whole tissue graft (e.g., kidney, liver, lung, etc). In some embodiments, the subject has an autoimmune diseases, rheumatological diseases, type 1 diabetes, and/or asthma.

Also disclosed is a method of treating autoimmunity in a subject that involves administering to the subject an effective amount of the HDAC6-inhibited Treg cells. Also disclosed is a method of preventing rejection of solid organ allografts and off-the-shelf CAR-T cells in a subject that involves administering to the subject an effective amount of the HDAC6-inhibited Treg cells. Also disclosed is a method of preventing rejection of CAR-T cells in a subject that involves engineering the disclosed HDAC6-inhibited Treg cells with the CAR polypeptide to produce HDAC6-inhibited CAR-Tregs.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A to 1D show HDAC6 inhibition significantly increases human Treg proliferation and expansion. FIG. 1A show purified, human Tregs stimulated by allogeneic, monocyte-derived dendritic cells for 5-6 days, with HDTK032 or DMSO added once on day 0. The medium was also supplemented with IL-2 and IL-15. Bar graph shows HDTK032 increases Tregs numbers (replicate means±SEM), compared to DMSO. Proliferation was analyzed by Cell Trace Violet dilution among $CD4^+$, $CD127^-$, $CD25^{bright}$ Tregs. FIG. 1B shows representative contour plots show proliferating, DC-allostimulated Tregs treated with HDTK032 or DMSO. n=3 independent experiments. FIG. 1C is a graph showing on-target alpha-tubulin acetylation of HDTK032 or DMSO treated Tregs. One representative experiment of 3 independent studies is shown. FIG. 1D shows the HDAC6 inhibitors, HDTK032 and Tubastatin, increase the frequency of antigen-specific thymic Tregs after 12 days of culture with allogeneic moDCs. One representative donor Treg expansion of 4 independent experiments is shown. *P<0.05.

FIG. 3A contains representative contour plots showing the purity (>95% pure) of the injected Tregs ($CD4^+$, $CD127^-$, $CD25^{bright}$, Foxp3+) for each experimental condition. FIG. 3B shows graft rejection scores at day +21 assessed by a blinded, expert pathologist are shown. Pooled data from 3 independent experiments, with up to 9 mice per experimental group. FIG. 3C contains representative H&E sections from day +21. P=0.001-0.01, *P=0.0001-0.001. NS=not significant.

FIG. 3D contains representative IHC images showing Th1, Th2, and Tregs in the harvest skin grafts among each experimental condition. Pooled data from 3 independent experiments, with up to 9 mice per experimental group. *P<0.05. NS=not significant.

FIGS. 5A and 5B contain a bar graph and representative contour plots showing the amount (means±SEM) of Th17 cells in the recipient spleens on day +21. FIGS. 5C and 5D contain a bar graph and representative contour plots showing the amount (means±SEM) of Tregs cells in the recipient spleens on day +21. Pooled data from 3 independent experiments, with up to 9 mice per experimental group. *P<0.05. NS=not significant.

FIGS. 6A and 6B is a bar graph and representative contour plots showing the amount (means±SEM) of Th1 cells in the recipient spleens on day +21. FIG. 6B is a bar graph showing the amount (means±SEM) of Th2 cells in the recipient spleens on day +21. Pooled data from 3 independent experiments, with up to 9 mice per experimental group. *P<0.05. NS=not significant.

DETAILED DESCRIPTION

Figure 1A:
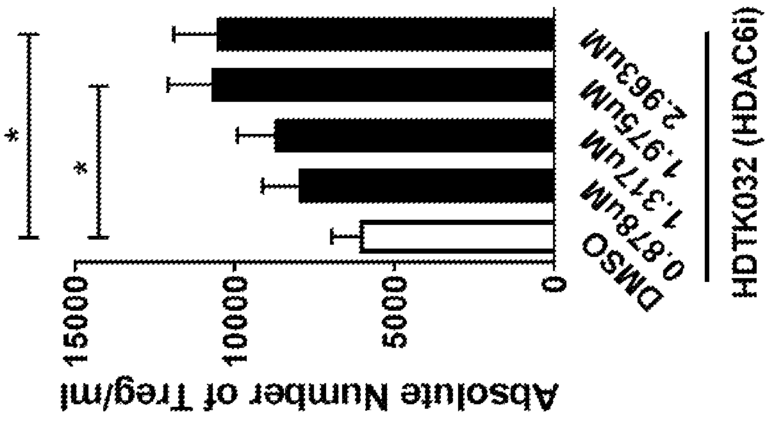

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

The term "amino acid sequence" refers to a list of abbreviations, letters, characters or words representing amino acid residues. The amino acid abbreviations used herein are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

The term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class from any species, including any of the human classes: IgG, IgM, IgA, IgD, and IgE. In exemplary embodiments, antibodies used with the methods and compositions described herein are derivatives of the IgG class. In addition to intact immunoglobulin molecules, also included in the term "antibodies" are fragments or polymers of those immunoglobulin molecules, and human or humanized versions of immunoglobulin molecules that selectively bind the target antigen.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')2, scFv, Fv, dsFv diabody, Fc, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

The term "antigen binding site" refers to a region of an antibody that specifically binds an epitope on an antigen.

The term "aptamer" refers to oligonucleic acid or peptide molecules that bind to a specific target molecule. These molecules are generally selected from a random sequence pool. The selected aptamers are capable of adapting unique tertiary structures and recognizing target molecules with high affinity and specificity. A "nucleic acid aptamer" is a DNA or RNA oligonucleic acid that binds to a target molecule via its conformation, and thereby inhibits or suppresses functions of such molecule. A nucleic acid aptamer may be constituted by DNA, RNA, or a combination thereof. A "peptide aptamer" is a combinatorial protein molecule with a variable peptide sequence inserted within a constant scaffold protein. Identification of peptide aptamers is typically performed under stringent yeast dihybrid conditions, which enhances the probability for the selected peptide aptamers to be stably expressed and correctly folded in an intracellular context.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "chimeric molecule" refers to a single molecule created by joining two or more molecules that exist separately in their native state. The single, chimeric molecule has the desired functionality of all of its constituent molecules. One type of chimeric molecules is a fusion protein.

The term "engineered antibody" refers to a recombinant molecule that comprises at least an antibody fragment comprising an antigen binding site derived from the variable domain of the heavy chain and/or light chain of an antibody and may optionally comprise the entire or part of the variable and/or constant domains of an antibody from any of the Ig classes (for example IgA, IgD, IgE, IgG, IgM and IgY).

The term "epitope" refers to the region of an antigen to which an antibody binds preferentially and specifically. A monoclonal antibody binds preferentially to a single specific epitope of a molecule that can be molecularly defined. In the present invention, multiple epitopes can be recognized by a multispecific antibody.

The term "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

The term "Fab fragment" refers to a fragment of an antibody comprising an antigen-binding site generated by cleavage of the antibody with the enzyme papain, which cuts at the hinge region N-terminally to the inter-H-chain disulfide bond and generates two Fab fragments from one antibody molecule.

The term "F(ab')2 fragment" refers to a fragment of an antibody containing two antigen-binding sites, generated by cleavage of the antibody molecule with the enzyme pepsin which cuts at the hinge region C-terminally to the inter-H-chain disulfide bond.

The term "Fc fragment" refers to the fragment of an antibody comprising the constant domain of its heavy chain.

The term "Fv fragment" refers to the fragment of an antibody comprising the variable domains of its heavy chain and light chain.

"Gene construct" refers to a nucleic acid, such as a vector, plasmid, viral genome or the like which includes a "coding sequence" for a polypeptide or which is otherwise transcribable to a biologically active RNA (e.g., antisense, decoy, ribozyme, etc), may be transfected into cells, e.g. in certain embodiments mammalian cells, and may cause expression of the coding sequence in cells transfected with the construct. The gene construct may include one or more regulatory elements operably linked to the coding sequence, as well as intronic sequences, polyadenylation sites, origins of replication, marker genes, etc.

The term "linker" is art-recognized and refers to a molecule or group of molecules connecting two compounds, such as two polypeptides. The linker may be comprised of a single linking molecule or may comprise a linking molecule and a spacer molecule, intended to separate the linking molecule and a compound by a specific distance.

The term "multivalent antibody" refers to an antibody or engineered antibody comprising more than one antigen recognition site. For example, a "bivalent" antibody has two antigen recognition sites, whereas a "tetravalent" antibody has four antigen recognition sites. The terms "monospecific", "bispecific", "trispecific", "tetraspecific", etc. refer to the number of different antigen recognition site specificities (as opposed to the number of antigen recognition sites) present in a multivalent antibody. For example, a "monospecific" antibody's antigen recognition sites all bind the same epitope. A "bispecific" antibody has at least one antigen recognition site that binds a first epitope and at least one antigen recognition site that binds a second epitope that is different from the first epitope. A "multivalent monospecific" antibody has multiple antigen recognition sites that all bind the same epitope. A "multivalent bispecific" antibody has multiple antigen recognition sites, some number of which bind a first epitope and some number of which bind a second epitope that is different from the first epitope.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

The term "operably linked to" refers to the functional relationship of a nucleic acid with another nucleic acid sequence. Promoters, enhancers, transcriptional and translational stop sites, and other signal sequences are examples of nucleic acid sequences operably linked to other sequences. For example, operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The terms "peptide," "protein," and "polypeptide" are used interchangeably to refer to a natural or synthetic molecule comprising two or more amino acids linked by the carboxyl group of one amino acid to the alpha amino group of another.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The terms "polypeptide fragment" or "fragment", when used in reference to a particular polypeptide, refers to a polypeptide in which amino acid residues are deleted as compared to the reference polypeptide itself, but where the remaining amino acid sequence is usually identical to that of the reference polypeptide. Such deletions may occur at the amino-terminus or carboxy-terminus of the reference polypeptide, or alternatively both. Fragments typically are at least about 5, 6, 8 or 10 amino acids long, at least about 14 amino acids long, at least about 20, 30, 40 or 50 amino acids long, at least about 75 amino acids long, or at least about 100, 150, 200, 300, 500 or more amino acids long. A fragment can retain one or more of the biological activities of the reference polypeptide. In various embodiments, a fragment may comprise an enzymatic activity and/or an interaction site of the reference polypeptide. In another embodiment, a fragment may have immunogenic properties.

The term "protein domain" refers to a portion of a protein, portions of a protein, or an entire protein showing structural integrity; this determination may be based on amino acid composition of a portion of a protein, portions of a protein, or the entire protein.

The term "single chain variable fragment or scFv" refers to an Fv fragment in which the heavy chain domain and the light chain domain are linked. One or more scFv fragments may be linked to other antibody fragments (such as the constant domain of a heavy chain or a light chain) to form antibody constructs having one or more antigen recognition sites.

A "spacer" as used herein refers to a peptide that joins the proteins comprising a fusion protein. Generally a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule.

The term "specifically binds", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8 M^{-1}$, $10^9$ $M^{-1}$, $10^{10}$ $M^{-1}$, $10^{11}$ $M^{-1}$ and $10^{12}$ $M^{-1}$ or more) with that second molecule.

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule. Typically specific delivery results in a much stronger association between the delivered molecule and cells bearing the target molecule than between the delivered molecule and cells lacking the target molecule.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The terms "transformation" and "transfection" mean the introduction of a nucleic acid, e.g., an expression vector, into a recipient cell including introduction of a nucleic acid to the chromosomal DNA of said cell.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "variant" refers to an amino acid or peptide sequence having conservative amino acid substitutions, non-conservative amino acid substitutions (i.e. a degenerate variant), substitutions within the wobble position of each codon (i.e. DNA and RNA) encoding an amino acid, amino acids added to the C-terminus of a peptide, or a peptide having 60%, 70%, 80%, 90%, 95%, 96%, 97%, 98%, 99% sequence identity to a reference sequence.

The term "vector" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element).

CAR Polypeptides

The disclosed methods can be used to produce chimeric antigen receptor (CAR) T cells containing CAR polypeptides. A CAR polypeptide is generally made up of three domains: an ectodomain, a transmembrane domain, and an endodomain. The ectodomain is responsible for antigen recognition. It also optionally contains a signal peptide (SP) so that the CAR can be glycosylated and anchored in the cell membrane of the immune effector cell. The transmembrane domain (TD), is as its name suggests, connects the ectodomain to the endodomain and resides within the cell membrane when expressed by a cell. The endodomain is the business end of the CAR that transmits an activation signal to the immune effector cell after antigen recognition. For example, the endodomain can contain an intracellular signaling domain (ISD) and optionally a co-stimulatory signaling region (CSR). CAR polypeptides generally incorporate an antigen recognition domain from the single-chain variable fragments (scFv) of a monoclonal antibody (mAb) with transmembrane signaling motifs involved in lymphocyte activation (Sadelain M, et al. Nat Rev Cancer 2003 3:35-45).

A "signaling domain (SD)" generally contains immunoreceptor tyrosine-based activation motifs (ITAMs) that activate a signaling cascade when the ITAM is phosphorylated. The term "co-stimulatory signaling region (CSR)" refers to intracellular signaling domains from costimulatory protein receptors, such as CD28, 41BB, and ICOS, that are able to enhance T-cell activation by T-cell receptors.

Additional CAR constructs are described, for example, in Fresnak A D, et al. Engineered T cells: the promise and challenges of cancer immunotherapy. Nat Rev Cancer. 2016 Aug. 23; 16(9):566-81, which is incorporated by reference in its entirety for the teaching of these CAR models.

For example, the CAR can be a TRUCK, Universal CAR, Self-driving CAR, Armored CAR, Self-destruct CAR, Conditional CAR, Marked CAR, TenCAR, Dual CAR, or sCAR.

CAR T cells engineered to be resistant to immunosuppression (Armored CARs) may be genetically modified to no longer express various immune checkpoint molecules (for example, cytotoxic T lymphocyte-associated antigen 4 (CTLA4) or programmed cell death protein 1 (PD1)), with an immune checkpoint switch receptor, or may be administered with a monoclonal antibody that blocks immune checkpoint signaling.

A self-destruct CAR may be designed using RNA delivered by electroporation to encode the CAR. Alternatively, inducible apoptosis of the T cell may be achieved based on ganciclovir binding to thymidine kinase in gene-modified lymphocytes or the more recently described system of activation of human caspase 9 by a small-molecule dimerizer.

A conditional CAR T cell is by default unresponsive, or switched 'off', until the addition of a small molecule to complete the circuit, enabling full transduction of both signal 1 and signal 2, thereby activating the CAR T cell. Alternatively, T cells may be engineered to express an adaptor-specific receptor with affinity for subsequently administered secondary antibodies directed at target antigen.

A tandem CAR (TanCAR) T cell expresses a single CAR consisting of two linked single-chain variable fragments (scFvs) that have different affinities fused to intracellular co-stimulatory domain(s) and a CD3ζ domain. TanCAR T cell activation is achieved only when target cells co-express both targets.

A dual CAR T cell expresses two separate CARs with different ligand binding targets; one CAR includes only the CD3ζ domain and the other CAR includes only the co-stimulatory domain(s). Dual CAR T cell activation requires co-expression of both targets.

A safety CAR (sCAR) consists of an extracellular scFv fused to an intracellular inhibitory domain. sCAR T cells co-expressing a standard CAR become activated only when encountering target cells that possess the standard CAR target but lack the sCAR target.

The antigen recognition domain of the disclosed CAR is usually an scFv. There are however many alternatives. An antigen recognition domain from native T-cell receptor (TCR) alpha and beta single chains have been described, as have simple ectodomains (e.g. CD4 ectodomain to recognize HIV infected cells) and more exotic recognition components such as a linked cytokine (which leads to recognition of cells bearing the cytokine receptor). In fact almost anything that binds a given target with high affinity can be used as an antigen recognition region.

The endodomain is the business end of the CAR that after antigen recognition transmits a signal to the immune effector cell, activating at least one of the normal effector functions of the immune effector cell. Effector function of a T cell, for example, may be cytolytic activity or helper activity including the secretion of cytokines. Therefore, the endodomain may comprise the "intracellular signaling domain" of a T cell receptor (TCR) and optional co-receptors. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal.

Cytoplasmic signaling sequences that regulate primary activation of the TCR complex that act in a stimulatory manner may contain signaling motifs which are known as immunoreceptor tyrosine-based activation motifs (ITAMs). Examples of ITAM containing cytoplasmic signaling sequences include those derived from CD8, CD3ζ, CD3δ, CD3γ, CD3ε, CD32 (Fc gamma RIIa), DAP10, DAP12, CD79a, CD79b, FcγRIγ, FcγRIIIγ, FcεRIβ(FCERIB), and FcεRIγ (FCERIG).

In particular embodiments, the intracellular signaling domain is derived from CD3 zeta (CD3ζ) (TCR zeta, GenBank accno. BAG36664.1). T-cell surface glycoprotein CD3 zeta (CD3ζ) chain, also known as T-cell receptor T3 zeta chain or CD247 (Cluster of Differentiation 247), is a protein that in humans is encoded by the CD247 gene.

First-generation CARs typically had the intracellular domain from the CD3ζ chain, which is the primary transmitter of signals from endogenous TCRs. Second-generation CARs add intracellular signaling domains from various costimulatory protein receptors (e.g., CD28, 41BB, ICOS) to the endodomain of the CAR to provide additional signals to the T cell. More recent, third-generation CARs combine multiple signaling domains to further augment potency. T cells grafted with these CARs have demonstrated improved expansion, activation, persistence, and tumor-eradicating efficiency independent of costimulatory receptor/ligand interaction (Imai C, et al. Leukemia 2004 18:676-84; Maher J, et al. Nat Biotechnol 2002 20:70-5).

For example, the endodomain of the CAR can be designed to comprise the CD3 ζ signaling domain by itself or combined with any other desired cytoplasmic domain(s) useful in the context of the CAR of the invention. For example, the cytoplasmic domain of the CAR can comprise a CD3 ζ chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, ICOS, lymphocyte function-associated antigen-1 (LFA-1), CD2, CD7, LIGHT, NKG2C, B7-H3, and a ligand that specifically binds with CD123, CD8, CD4, b2c, CD80, CD86, DAP10, DAP12, MyD88, BTNL3, and NKG2D. Thus, while the CAR is exemplified primarily with CD28 as the co-stimulatory signaling element, other costimulatory elements can be used alone or in combination with other co-stimulatory signaling elements.

In some embodiments, the CAR comprises a hinge sequence. A hinge sequence is a short sequence of amino acids that facilitates antibody flexibility (see, e.g., Woof et al., Nat. Rev. Immunol., 4(2): 89-99 (2004)). The hinge sequence may be positioned between the antigen recognition moiety (e.g., scFv) and the transmembrane domain. The hinge sequence can be any suitable sequence derived or obtained from any suitable molecule. In some embodiments, for example, the hinge sequence is derived from a CD8a molecule or a CD28 molecule.

The transmembrane domain may be derived either from a natural or from a synthetic source. Where the source is natural, the domain may be derived from any membrane-bound or transmembrane protein. For example, the transmembrane region may be derived from (i.e. comprise at least the transmembrane region(s) of) the alpha, beta or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, or CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R $\alpha$, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, and PAG/Cbp. Alternatively the transmembrane domain may be synthetic, in which case it will comprise predominantly hydrophobic residues such as leucine and valine. In some cases, a triplet of phenylalanine, tryptophan and valine will be found at each end of a synthetic transmembrane domain. A short oligo- or polypeptide linker, such as between 2 and 10 amino acids in length, may form the linkage between the transmembrane domain and the endoplasmic domain of the CAR.

In some embodiments, the CAR has more than one transmembrane domain, which can be a repeat of the same transmembrane domain, or can be different transmembrane domains.

In some embodiments, the CAR is a multi-chain CAR, as described in WO2015/039523, which is incorporated by reference for this teaching. A multi-chain CAR can comprise separate extracellular ligand binding and signaling domains in different transmembrane polypeptides. The signaling domains can be designed to assemble in juxtamembrane position, which forms flexible architecture closer to natural receptors, that confers optimal signal transduction. For example, the multi-chain CAR can comprise a part of an FCERI alpha chain and a part of an FCERI beta chain such that the FCERI chains spontaneously dimerize together to form a CAR.

In some embodiments, the antigen recognition domain is single chain variable fragment (scFv) antibody. The affinity/specificity of an scFv is driven in large part by specific sequences within complementarity determining regions (CDRs) in the heavy ($V_H$) and light ($V_L$) chain. Each $V_H$ and $V_L$ sequence will have three CDRs (CDR1, CDR2, CDR3).

In some embodiments, the antigen recognition domain is derived from natural antibodies, such as monoclonal antibodies. In some cases, the antibody is human. In some cases, the antibody has undergone an alteration to render it less immunogenic when administered to humans. For example, the alteration comprises one or more techniques selected from the group consisting of chimerization, humanization, CDR-grafting, deimmunization, and mutation of framework amino acids to correspond to the closest human germline sequence.

Also disclosed are bi-specific CARs that target two antigens. Also disclosed are CARs designed to work only in conjunction with another CAR that binds a different antigen. For example, in these embodiments, the endodomain of the disclosed CAR can contain only a signaling domain (SD) or a co-stimulatory signaling region (CSR), but not both. The second CAR (or endogenous T-cell) provides the missing signal if it is activated. For example, if the disclosed CAR contains an SD but not a CSR, then the immune effector cell containing this CAR is only activated if another CAR (or T-cell) containing a CSR binds its respective antigen. Likewise, if the disclosed CAR contains a CSR but not a SD, then the immune effector cell containing this CAR is only activated if another CAR (or T-cell) containing an SD binds its respective antigen.

A number of embodiments of the invention have been described. Nevertheless, it will be understood that various modifications may be made without departing from the spirit and scope of the invention. Accordingly, other embodiments are within the scope of the following claims.

EXAMPLES

Figure 1B:
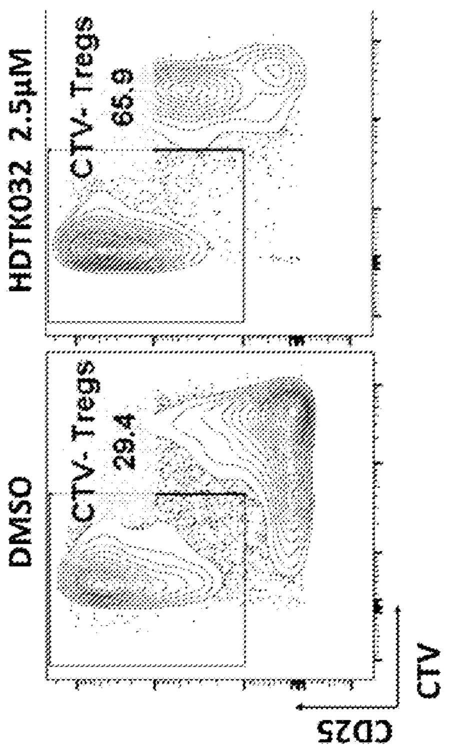
Figure 1C:
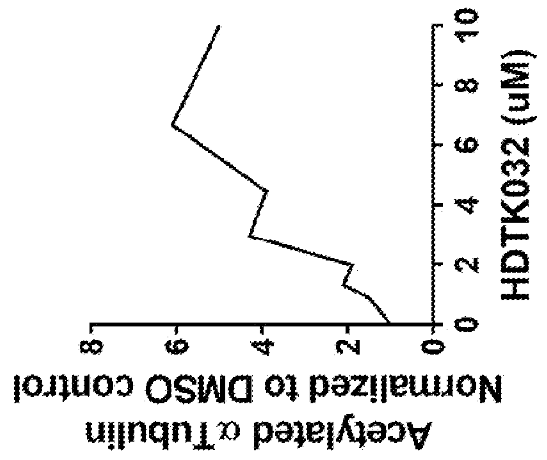

Example 1: HDAC6-Inhibited Human Tregs Prevent Allograft Rejection and Suppress Pathogenic Th1/Th17 Cells Results HDAC6 inhibition significantly increases human Treg proliferation and expansion. HDAC6-deficient mice are known to generate increased amounts of Tregs, both at stead-state in vivo and after polyclonal stimulation in vitro. However, such findings have never been translated to human immunity. Human nTregs ($CD4^+$, $CD127^-$, CD25+) were purified by magnetic bead isolation, stimulated with allogeneic moDCs, supplemented with IL-2, and treated with HDTK032, a selective and potent HDAC6 inhibitor, or DMSO (<0.01%) vehicle control once on day 0. After 5-6 days of culture, the nTregs were harvested and enumerated. HDTK032 significantly increased the amount of nTregs (FIG. 1A). Similarly, the proliferative capacity of the HDAC6-inhibited nTregs was increased as demonstrated by robust CellTrace™ Violet dilution (FIG. 1B). We confirmed on-target inhibition of HDAC6 by HDTK032 in treated nTregs, as demonstrated by an increase in the amount of acetylated $\alpha$-tubulin (FIG. 10). Using the limiting dilution assay (LDA) we measured the precise frequency of allo-specific nTregs after stimulation with unrelated moDCs for 12 days. For these experiments, the HDAC6 inhibitors, HDTK032 and tubastatin, were compared against DMSO. Overall, the mean fold expansion was approximately 130-fold with either HDAC6 inhibitor compared to DMSO (FIG.

1D). The HDAC6 inhibitors improved such antigen-specific nTreg expansion using cells from 4 independent healthy donors.

Figure 2:
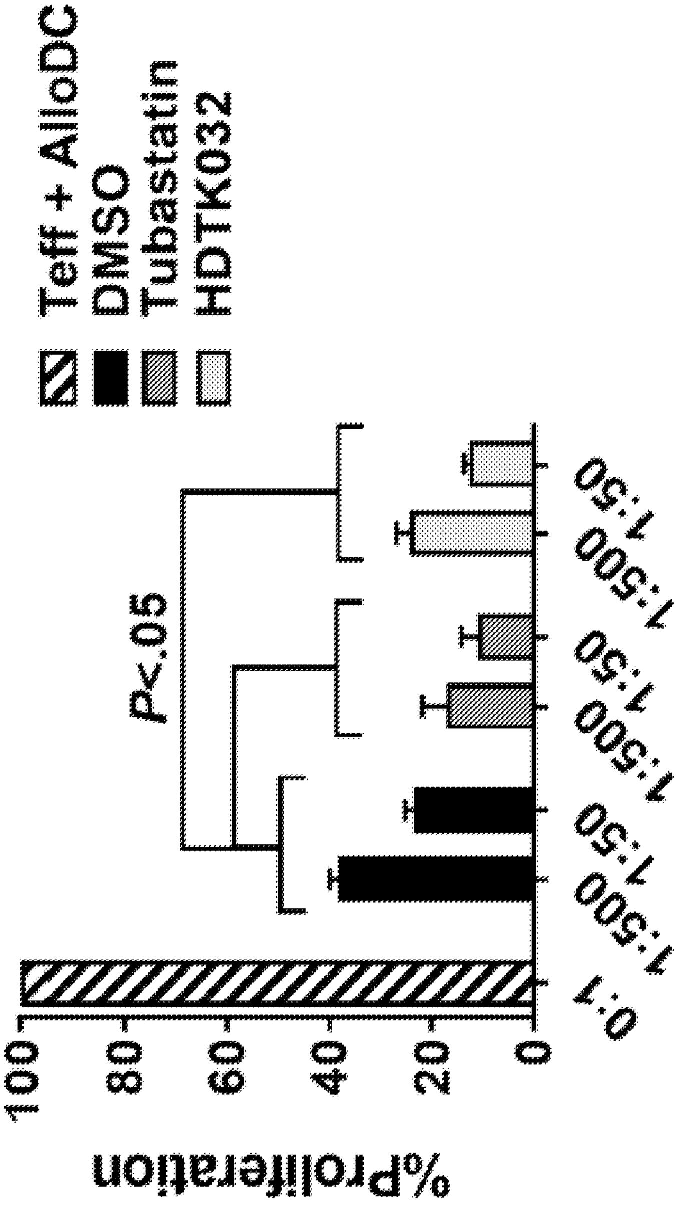
FIG. 2 shows HDAC6 inhibition significantly improves human Treg suppressive potency. The suppressive capacity of DC-allostimulated thymic Tregs previously exposed to HDTK032, tubastatin, or DMSO was tested at different ratios of Treg to T cell responders stimulated by fresh allogeneic DCs (DC:responder T cell ratio of 1:30) in mixed leukocyte reactions. No additional drugs or DMSO were added to the medium. Bar graph shows Treg proliferation (replicate means±SEM) based on [$^3$H]thymidine incorporation on day 6. Data are from one representative experiment of 3 independent studies performed.

HDAC6 inhibition significantly improves human Treg suppressive potency. Next we investigated whether HDAC6 blockade impacted nTreg function. Purified nTregs were stimulated with allogeneic moDCs plus IL-2 while exposed to tubastatin, HDTK032, or DMSO for 5 days. The nTregs were harvested and cultured with autologous T cells (nTreg:T cell ratio 1:500 or 1:50) targeting fresh allogeneic moDCs. No additional drugs were added to the secondary cultures. While DMSO-treated, antigen-specific nTregs were suppressive, the tubastatin- and HDTK032-treated nTregs were significantly more potent (FIG. 2).

Figure 3A:
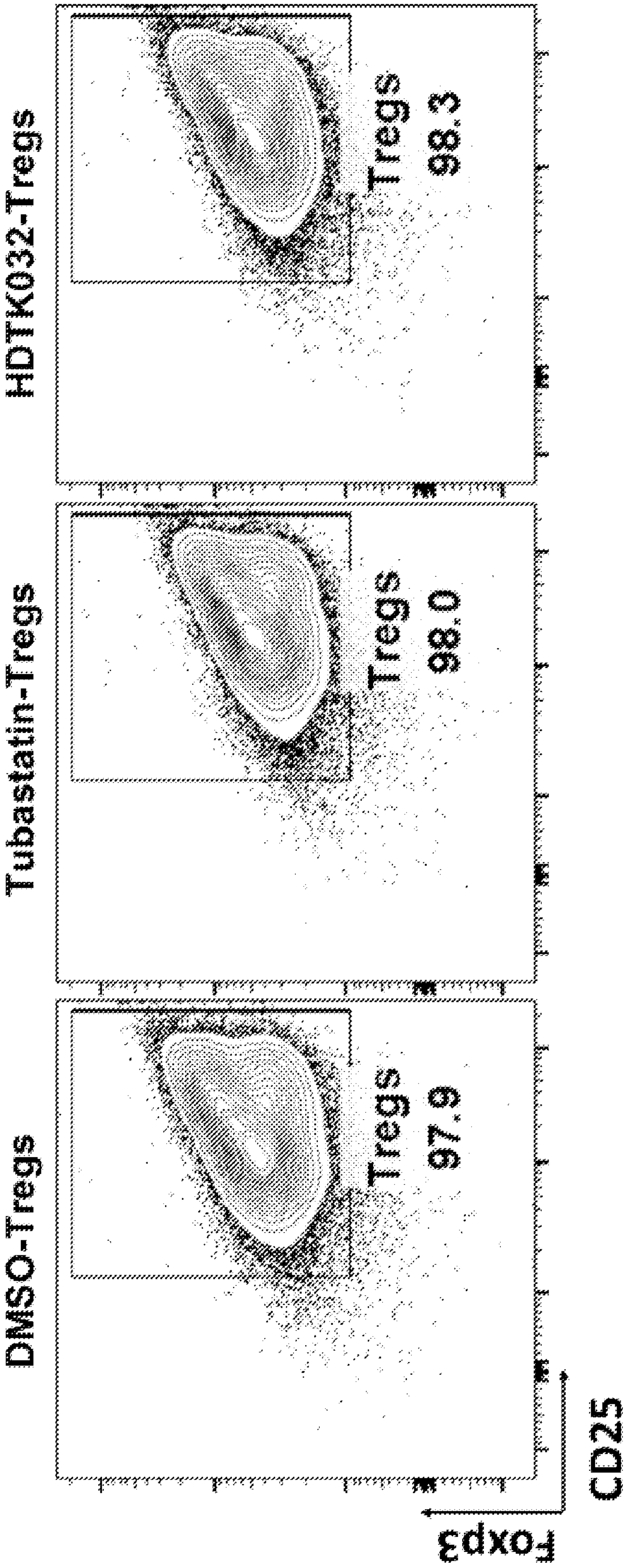
FIGS. 3A to 3C show adoptive transfer of HDAC6-inhibited human Tregs significantly reduces allograft rejection. NSG mice received a 1 $cm^2$ split thickness human skin graft. After 30 days of rest to permit engraftment, $5\times10^6$ human PBMCs (allogeneic to the skin) were injected into the mice. A week prior to PBMC injection, Tregs from the PBMC donor were expanded with mature DCs from the skin donor (Treg:DC ratio 30:1) and cultured for 5-6 days in the presence of DMSO (<0.1%), tubastatin (1 μM), HDTK032 (2.5 μM). In coordination with the PBMC injection, recipient mice were also inoculated with CD25-bead purified, Tregs ($5\times10^4$) expanded with DMSO, tubastatin, HDTK032. A control group received PBMCs alone.
Figure 3B:
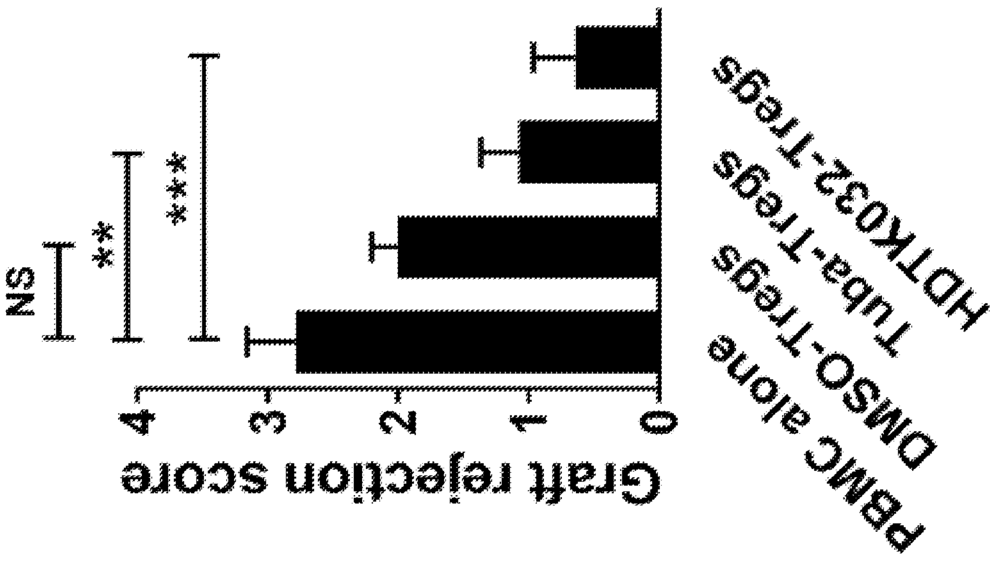
Figure 3C:
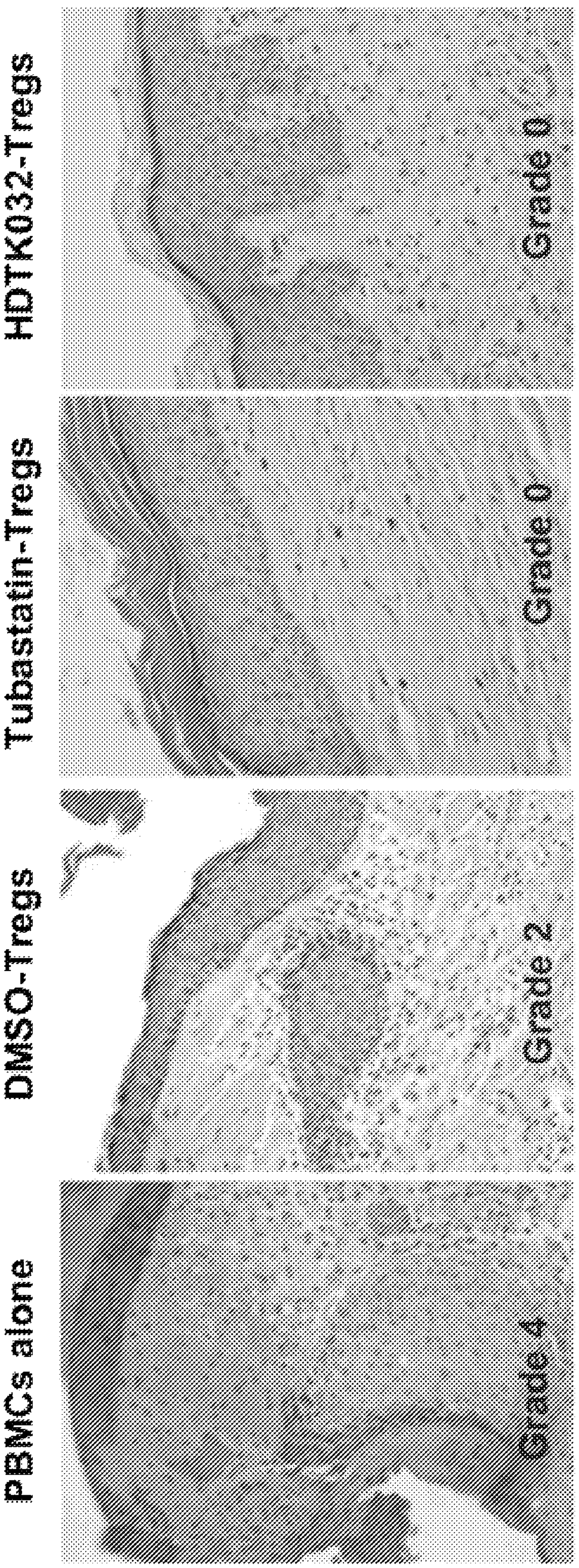
Figure 4C:
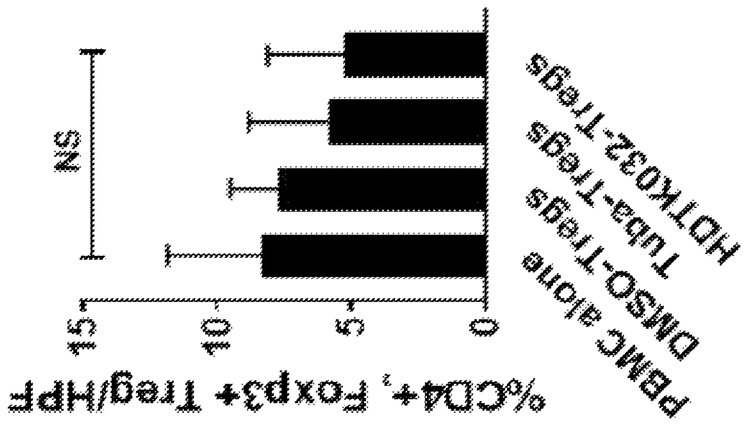
FIGS. 4A to 4D show HDAC6-inhibited human Tregs significantly reduce pathogenic Th1 cells in the allograft. NSG mice received a human skin graft, followed by allogeneic human PBMCs with or without DC-allostimulated Tregs pre-treated with DMSO, tubastatin, or HDTK032. On day +21, the recipient mice were humanely euthanized and the skin grafts were harvested. Immunohistochemistry was used to analyze Th1 ($CD4^+$, T-bet+), Th2 ($CD4^+$, GATA3+), and Treg ($CD4^+$, Foxp3+) in the skin grafts. A-C) Bar graphs show the amount of Th1, Th2, and Tregs (means±SEM) in the skin grafts at day +21.
Figure 4B:
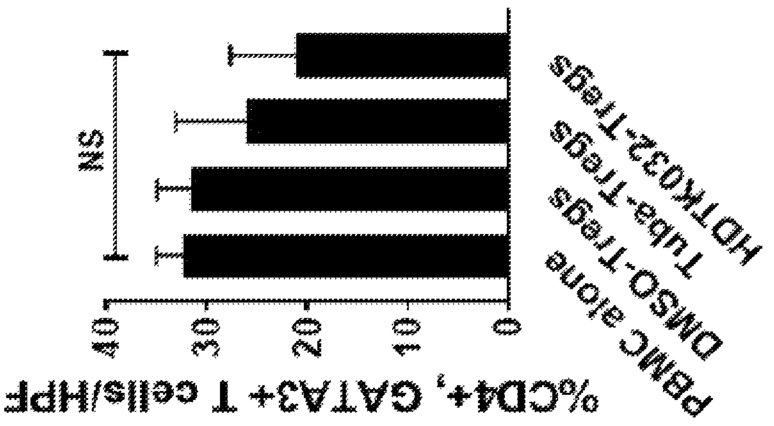
Figure 4A:
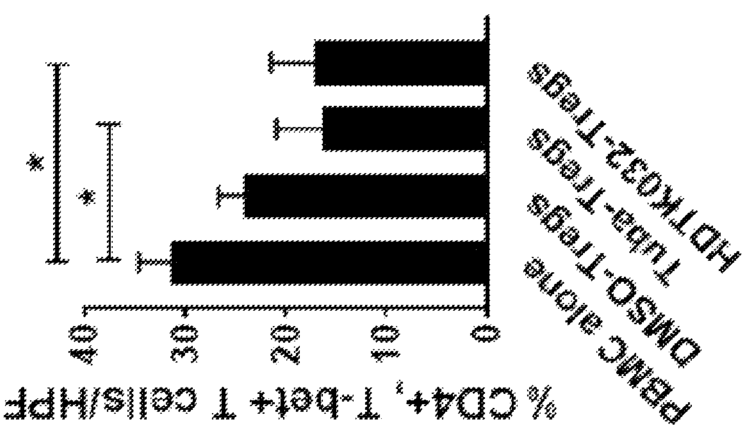
Figure 4D:
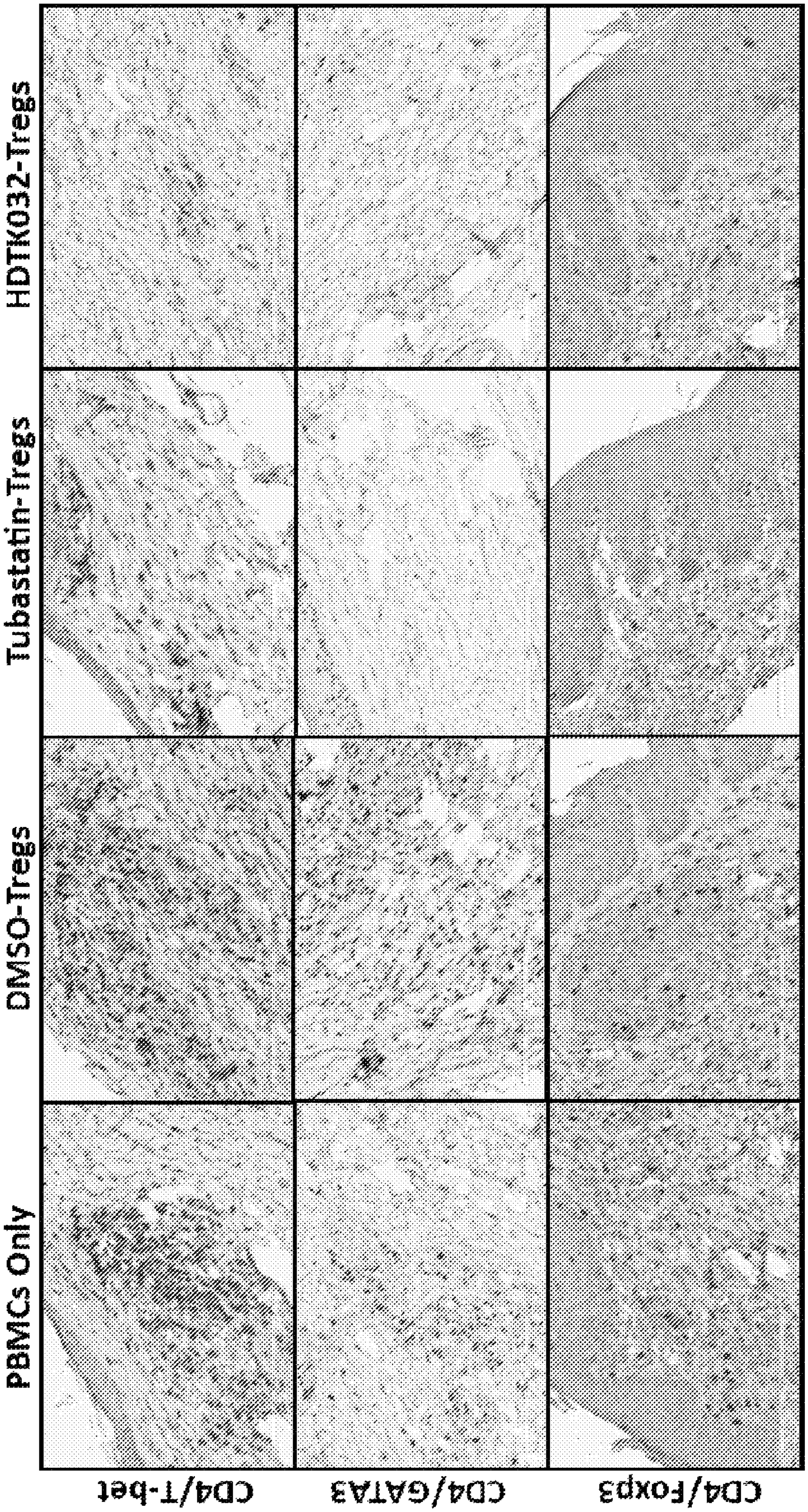
Figure 5A:
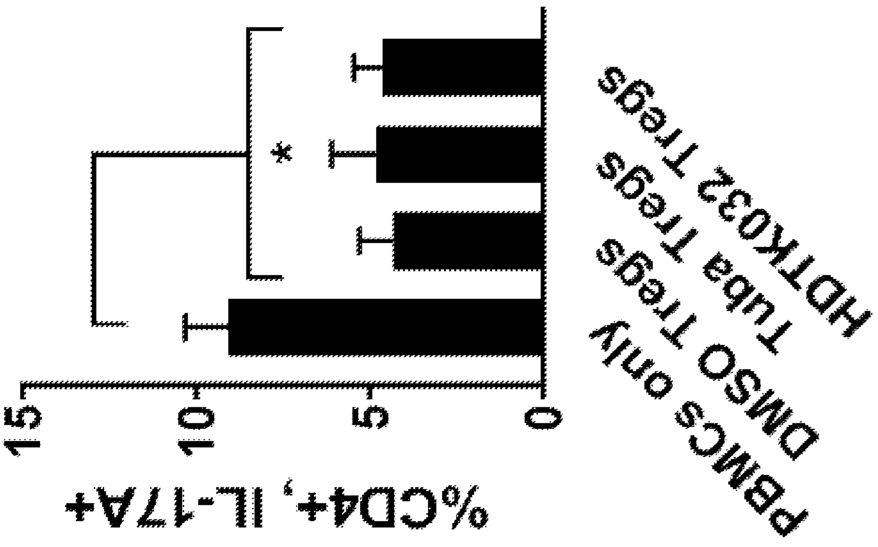
FIGS. 5A to 5D show pathogenic Th17 cells are decreased in the periphery among mice treated with HDAC6-inhibited human Tregs. NSG mice received a human skin graft, followed by allogeneic human PBMCs with or without DC-allostimulated Tregs pre-treated with DMSO, tubastatin, or HDTK032. Recipient spleens were harvested on day +21, stained for Th17s ($CD4^+$, $IL\text{-}17^+$) or Tregs ($CD4^+$, $CD127^-$, $CD25^{bright}$, $Foxp3^+$), and analyzed by flow cytometry.
Figure 5C:
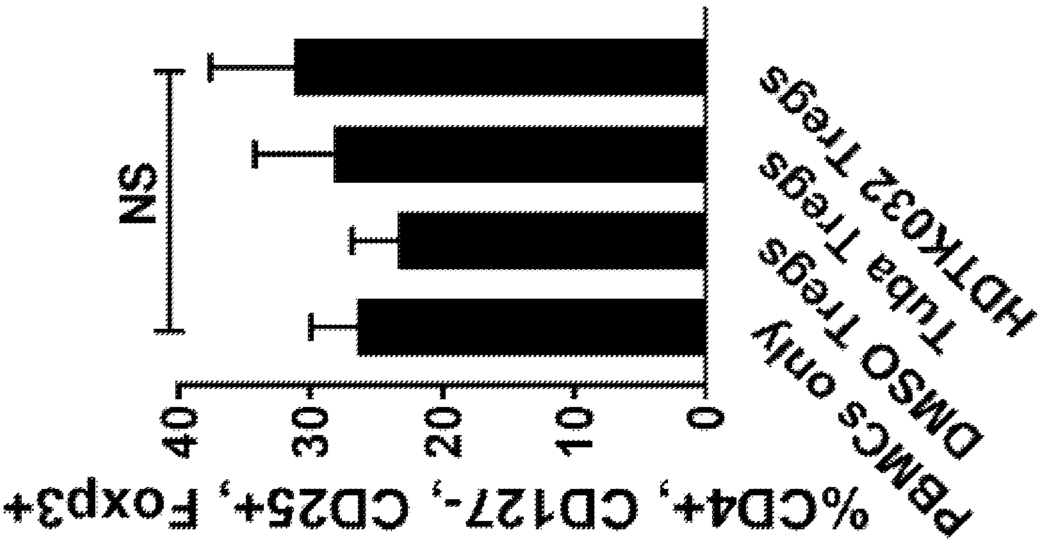
Figure 5B:
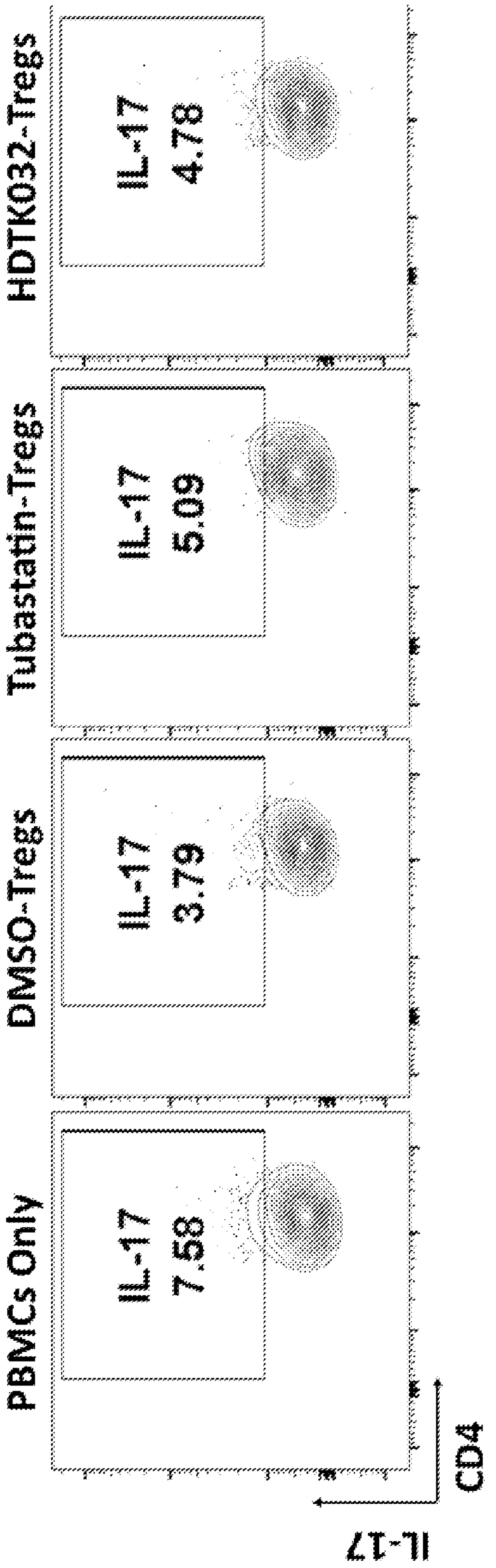
Figure 5D:
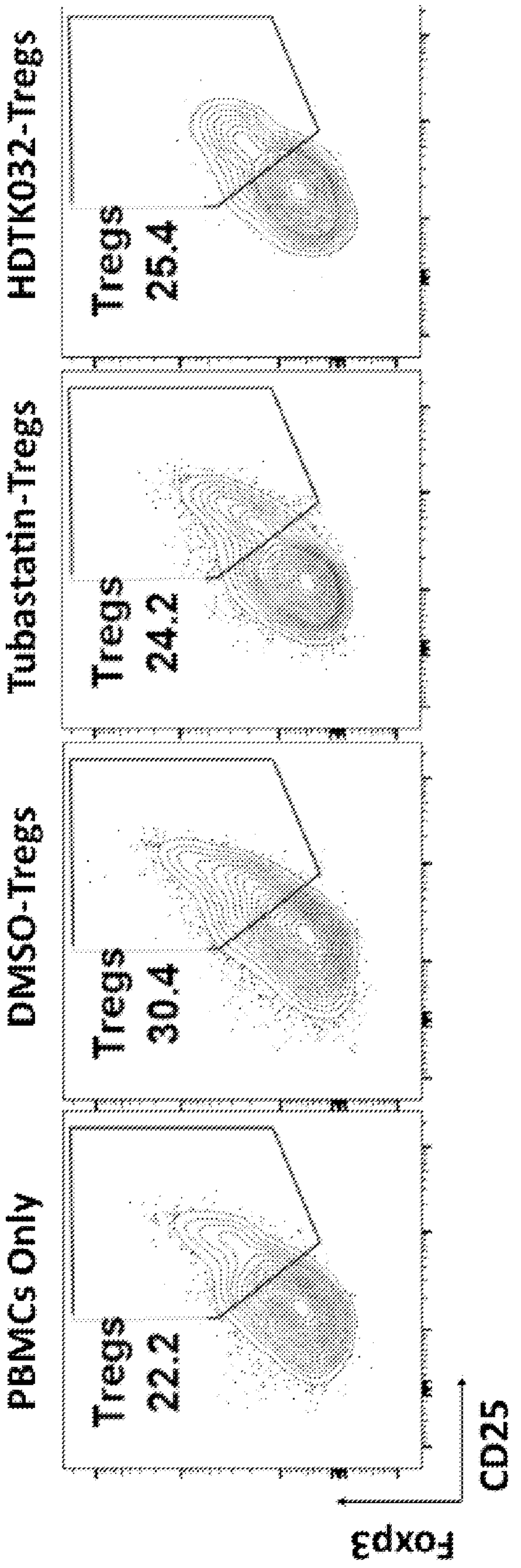
Figure 6A:
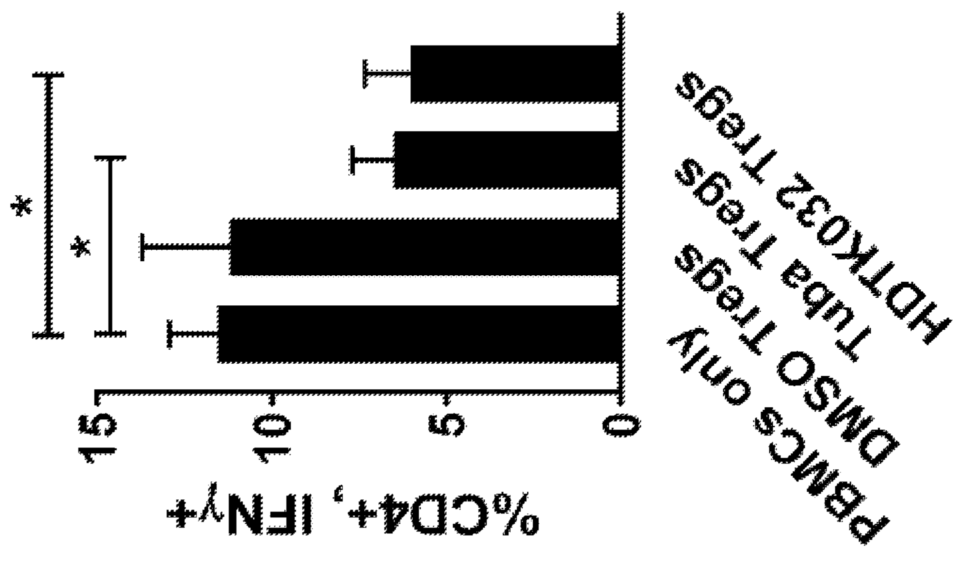
FIGS. 6A to 6C show circulating human Th1 cells are reduced after adoptive transfer of HDAC6-inhibited Tregs. NSG mice received a human skin graft, followed by allogeneic human PBMCs with or without DC-allostimulated Tregs pre-treated with DMSO, tubastatin, or HDTK032. Recipient spleens were harvested on day +21, stained for Th1s ($CD4^+$, $IFN\gamma^+$) or Th2s ($CD4^+$, $IL\text{-}4^+$), and analyzed by flow cytometry.
Figure 6B:
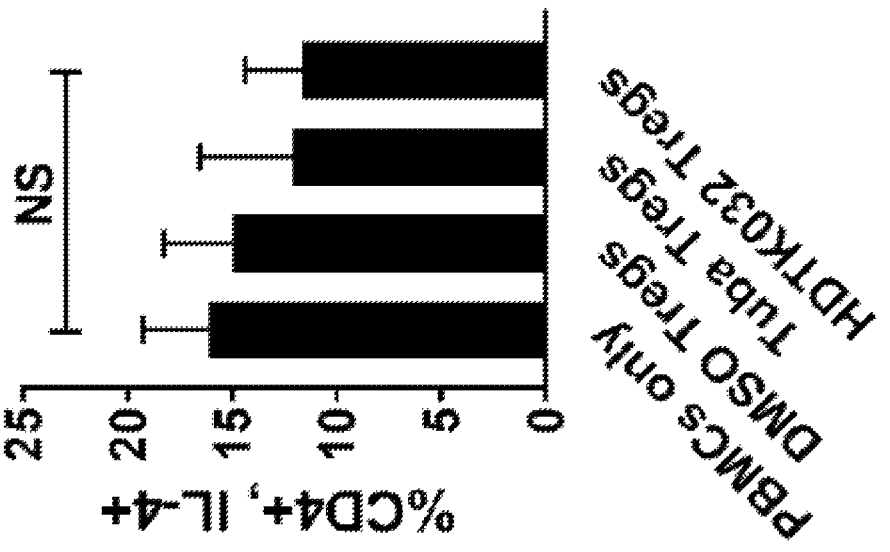
Figure 6C:
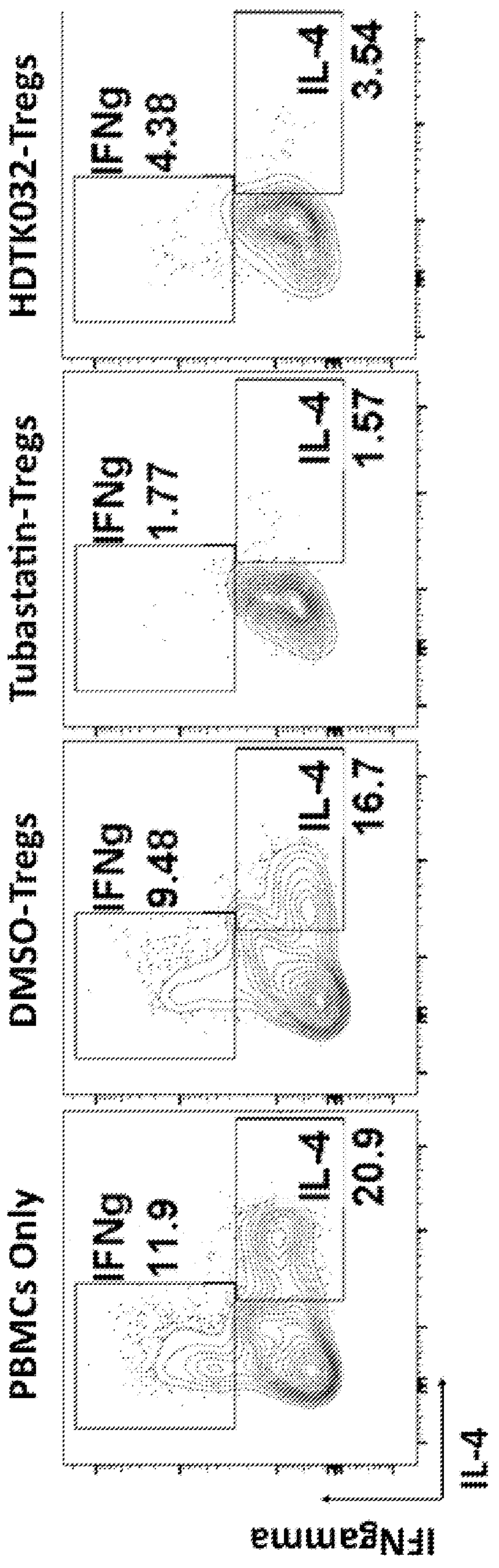
Figure 7:
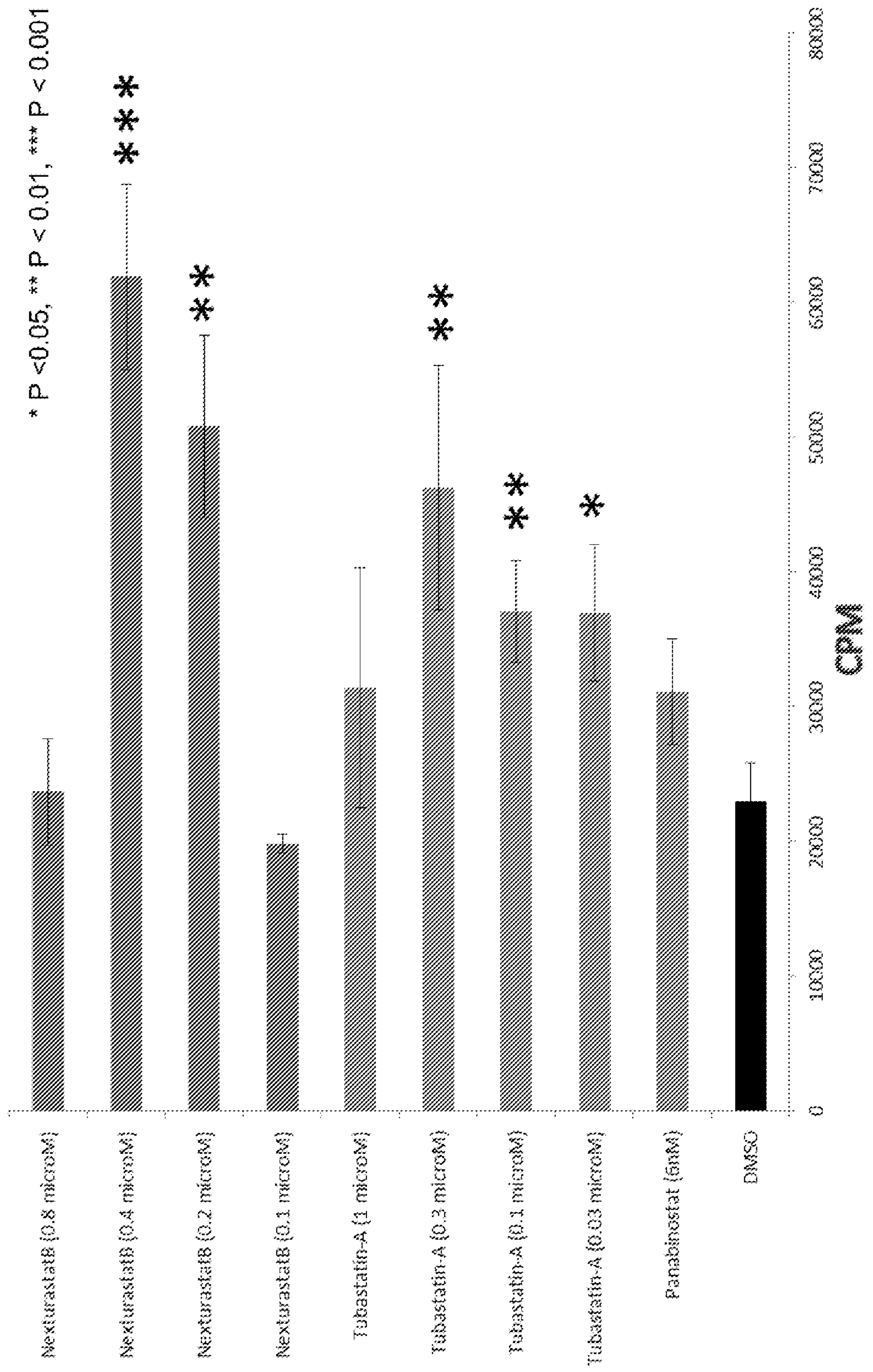
FIG. 7 shows the selective HDAC6 inhibitors nexurastat and tubastatin-A significantly enhance the proliferation and expansion of antigen-specific nTreg. Purified nTreg+allogeneic dendritic cells (DC)+IL-2+IL-15. Drugs added once on day 0. Proliferation measured as CPM on day +6.
Figure 8:
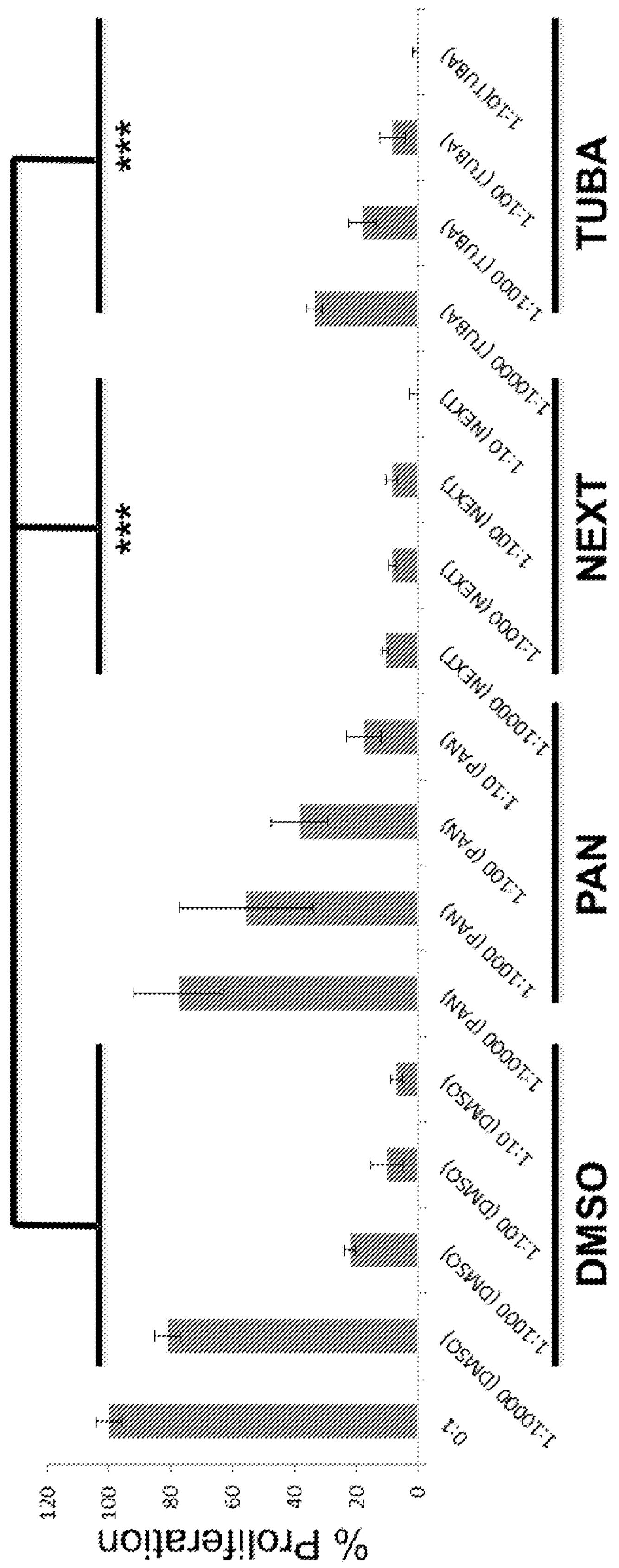
FIG. 8 shows antigen-specific nTreg expanded in the presence of HDAC6 inhibition exhibit increased suppressive potency. Suppression assay of DMSO- or HDAC-treated, antigen-specific nTreg in culture with 10:1 autologous T responders and allogeneic DCs. Proliferation measured on day +6. Nexturastat-B and Tubastatin significantly increase the suppressive function of nTreg. PAN=Panobinostat, NEXT=Nexturastat-B, TUBA=Tubastatin. DMSO is vehicle control.

Adoptive transfer of HDAC6-inhibited human Tregs significantly reduces allograft rejection in vivo. Human skin is a critical GVHD-target organ, and a highly immunogenic barrier organ. As such, we used an established skin xenograft model to test the potency of the human, HDAC6-inhibited nTreg in vivo. NSG mice were transplanted with a 1 cm2 human skin xenograft. The mice were rested for 30 days to heal, and during this time moDCs were generated from the skin donor to stimulate and expand allogeneic, antigen-specific nTregs. During the expansion, the donor Tregs were cultured with tubastatin, HDTK032, or DMSO. After 5-6 days of expansion, the human nTregs were harvested and prepared for infusion with a final product purity of >95% (FIG. 3A) based on $CD127^-$, $CD4^+$ T cell expression of CD25 and Foxp3. The skin-graft recipient mice were injected with 5×106 human PBMCs (autologous to the Tregs and allogeneic to the skin) with or without 5×104 DMSO-, tubastatin-, or HDTK032-treated nTregs. None of the mice received systemic therapy with tubastatin or HDTK032. The mice were humanely euthanized on day +21, and skin graft rejection was determined by a blinded, expert pathologist. While the effect by the DMSO-treated nTregs was modest and not significant, the tubastatin- and HDTK032-treated nTregs significantly reduced skin graft rejection compared to PBMCs alone (FIG. 3B,C).

HDAC6-inhibited human Tregs significantly reduce pathogenic Th1 cells in the allograft. Given the HDAC6-inhibited nTregs provided superior protection from human alloreactivity in vivo, we examined the T cell subsets within the skin graft by immunohistochemistry.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating graft versus host disease in a subject, comprising i) isolating PBMCs from the subject, ii) producing Tregs from the PBMCs according to a method comprising (a) purifying CD4+, CD127−, CD25+ Tregs from PBMCs by magnetic bead isolation, (b) stimulating the Tregs with allogeneic monocyte derived DCs, and (c) expanding the Tregs in a culture medium comprising IL-2 and an effective amount of an HDAC6-selective inhibitor for at least 5 days, and iii) transferring the treated Treg cells back to the subject.

2. The method of claim 1, wherein the subject is being treated with an organ transplant.

3. The method of claim 1, wherein the subject is being treated with recombinant or allogeneic immune effector cells.

4. The method of claim 2, wherein the method is being treated with an off-the shelf chimeric antigen receptor (CAR) T cell.

5. The method of claim 4, wherein the subject has an autoimmune disease.

6. The method of claim 1, wherein the Treg is engineered to express a CAR polypeptide.

* * * * *